(12) United States Patent
Yu et al.

(10) Patent No.: US 11,298,693 B2
(45) Date of Patent: Apr. 12, 2022

(54) METHOD AND CATALYST FOR SELECTIVE OLIGOMERIZATION OF ETHYLENE

(71) Applicant: PETROCHINA COMPANY LIMITED, Beijing (CN)

(72) Inventors: Buwei Yu, Beijing (CN); Tao Jiang, Beijing (CN); Sihan Wang, Beijing (CN); Hongling Chu, Beijing (CN); Yan Jiang, Beijing (CN); Hongliang Huo, Beijing (CN); Xianming Xu, Beijing (CN); Libo Wang, Beijing (CN); Huaiqi Shao, Beijing (CN); Yali Wang, Beijing (CN); Yuanyuan Cao, Beijing (CN); Tong Liu, Beijing (CN); Kecun Ma, Beijing (CN); Fuling Huang, Beijing (CN); Xiuhui Wang, Beijing (CN); Enhao Sun, Beijing (CN); Yulong Wang, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 288 days.

(21) Appl. No.: 16/446,454

(22) Filed: Jun. 19, 2019

(65) Prior Publication Data
US 2019/0388882 A1 Dec. 26, 2019

(30) Foreign Application Priority Data
Jun. 22, 2018 (CN) .......................... 201810648359.8

(51) Int. Cl.
| | | |
|---|---|---|
| B01J 31/18 | (2006.01) | |
| B01J 31/12 | (2006.01) | |
| B01J 31/14 | (2006.01) | |
| B01J 31/34 | (2006.01) | |
| B01J 31/36 | (2006.01) | |
| B01J 31/38 | (2006.01) | |
| C07C 2/32 | (2006.01) | |

(52) U.S. Cl.
CPC .......... *B01J 31/181* (2013.01); *B01J 31/121* (2013.01); *B01J 31/122* (2013.01); *B01J 31/143* (2013.01); *B01J 31/146* (2013.01); *B01J 31/34* (2013.01); *B01J 31/36* (2013.01); *B01J 31/38* (2013.01); *C07C 2/32* (2013.01); *B01J 2231/12* (2013.01); *B01J 2231/20* (2013.01)

(58) Field of Classification Search
None
See application file for complete search history.

(56) References Cited

U.S. PATENT DOCUMENTS

| 3,635,937 | A | 1/1972 | Bauer et al. |
|---|---|---|---|
| 3,676,523 | A | 7/1972 | Mason |
| 3,906,053 | A | 9/1975 | Lanier |
| 5,198,563 | A | 3/1993 | Reagen et al. |
| 5,550,305 | A | 8/1996 | Wu |
| 6,184,428 | B1 | 2/2001 | Zahoor et al. |
| 2019/0388882 | A1 | 12/2019 | Yu et al. |

FOREIGN PATENT DOCUMENTS

| CN | 101020695 A | 8/2007 |
|---|---|---|
| CN | 101041610 A | 9/2007 |
| CN | 101649012 A | 2/2010 |
| CN | 102906129 | 1/2013 |
| CN | 103059059 | 4/2013 |
| CN | 106582851 | 4/2017 |
| DE | 14 43 927 | 12/1968 |
| GB | 1 020 563 | 2/1966 |
| WO | WO-99/02472 | 1/1999 |
| WO | WO-2006/117048 A1 | 11/2006 |

OTHER PUBLICATIONS

Chinese Office Action and English Translation received for application No. 201810648359.8, dated Jul. 3, 2020, 8 pages.
Chinese Search Report and English Translation received for application No. 201810648359.8, dated Jul. 3, 2020, 3 pages.
Japanese Office Action and English Translation received for application No. 2019-112725, dated Jun. 9, 2020, 4 pages.
Small et al., "Iron-Based Catalysts with Exceptionally High Activities and Selectivities for Oligomerization of Ethylene to Linear α-Olefins," J. Am. Chem. Soc., 120, pp. 7143-7144 (Jul. 7, 1998).
Britovsek et al., "Novel Olefin Polymerization Catalysts Based on Iron and Cobalt," Chem. Commun., pp. 849-850 (Jan. 1, 1998).
Campbell et al., "Characterization of Porosity in Organic and Metal-Organic Macrocycles by Hyperpolarized 129 Xe NMR Spectroscopy", Organic Letters, vol. 7, No. 16, 4 Pages (2005).
Search Report and Written Opinion, Netherlands App. No. 2023317 (dated Mar. 18, 2020).

*Primary Examiner* — Yun Qian
(74) *Attorney, Agent, or Firm* — Foley & Lardner LLP

(57) ABSTRACT

The present disclosure provides a method and a catalyst for selective oligomerization of ethylene. The raw material for the catalyst consists of a dehydropyridine annulene-type ligand, a transition metal compound, and an organometallic compound in a molar ratio of 1:0.5-100:0.1-5000. The present disclosure also provides a method for selective oligomerization of ethylene accomplished by using the above-mentioned catalyst. The catalyst for selective oligomerization of ethylene has high catalytic activity, high selectivity for the target products 1-hexene and 1-octene, and low selectivity for 1-butene and 1-$C_{10}^+$.

10 Claims, No Drawings

METHOD AND CATALYST FOR SELECTIVE OLIGOMERIZATION OF ETHYLENE

CROSS-REFERENCE TO RELATED APPLICATIONS

This application claims the benefit of and priority to Chinese Patent Application No. 201810648359.8, filed Jun. 22, 2018, which is incorporated herein by reference in its entirety.

TECHNICAL FIELD

The invention relates to a catalyst, in particular to a catalyst for selective oligomerization of ethylene, belonging to the technical field of catalysts.

BACKGROUND

Linear alpha-olefins are important organic chemical materials, and are widely used in the fields of copolymerization to produce polyethylene, surfactants, lubricating oils and oil additives. The light component (C4-C8) can be used as a comonomer to copolymerize with ethylene to produce linear low-density polyethylene. In particular, 1-hexene and 1-octene with high-purity can significantly improve the abrasion resistance and other chemical and mechanical properties of linear low-density polyethylene. As the global economy continues to grow, the demand for polyethylene with high performance continues to grow, and the demand for 1-hexene and 1-octene continues to grow at an average annual rate of 5.4% or more.

Industrial production methods of 1-hexene and 1-octene mainly include paraffin cracking, ethylene oligomerization and extraction separation, and the ethylene oligomerization method is the main method for producing 1-hexene and 1-octene. For example, U.S. Pat. No. 6,184,428 discloses a nickel catalyst using a boron compound as a cocatalyst to catalyze the oligomerization of ethylene to give a mixture of linear alpha-olefins, wherein the content of 1-hexene is 22% and the content of 1-octene is 19%. The SHOP process (U.S. Pat. Nos. 3,676,523, 3,635,937) uses a similar catalytic system, and the content of 1-hexene is 21% and the content of 1-octene is 11% in the oligomerization product. In other typical ethylene oligomerization processes, such as Chevron process of Gulf Oil's (DE1443927) and the ethylene oligomerization process of Ethyl Corporation (BP/Amoco, U.S. Pat. No. 3,906,053), the content of 1-hexene and 1-octene is generally 13-25%. In ethylene oligomerization employing the iron-based catalysts reported by Brookhart et al. (J. Am. Chem. Soc., 1998, 120: 7143; Chem. Commun. 1998, 849; WO 99/02472), the content of 1-hexene and 1-octene is also low (<20%). The carbon number of linear alpha-olefins in these production processes is consistent with the Schulz-Flory distribution, which makes the content of 1-hexene and 1-octene in the oligomerization product not too high. If 1-hexene and 1-octene with high-purity are to be obtained, it needs to be separated by multi-column distillation, which has a complicated process route and huge equipment investment. Therefore, it is very important to find a production process for preparing 1-hexene and 1-octene with high selectivity.

Catalyzing high selectivity oligomerization of ethylene is the main method for the production of 1-hexene and 1-octene, wherein the catalyst is its key technology. The development of new catalytic system and study of its catalytic mechanism have been the hotspots and difficult problems in this field. In recent years, researchers have conducted extensive research on ethylene selective oligomerization technology and have achieved many important research results. For example, the chromium catalyst system is used for the trimerization of ethylene to prepare 1-hexene, and industrial production has also been realized (U.S. Pat. Nos. 5,550,305, 5,198,563), but the content of the main product 1-hexene is generally greater than 90%, and the content of 1-octene is very few (<3%).

SUMMARY

An object of the present disclosure is to provide a catalyst for selective oligomerization of ethylene with high catalyst activity, high selectivity for the target products 1-hexene and 1-octene, and low selectivity for 1-butene and $1\text{-}C_{10}^+$.

In order to achieve the above technical object, the present disclosure provides a catalyst for selective oligomerization of ethylene, and the raw material for the catalyst consists of: a dehydropyridine annulene-type ligand, a transition metal compound, and an organometallic compound in a molar ratio of 1:0.5-100:0.1-5000; wherein the dehydropyridine annulene-type ligand has a structural formula as shown in Formula I:

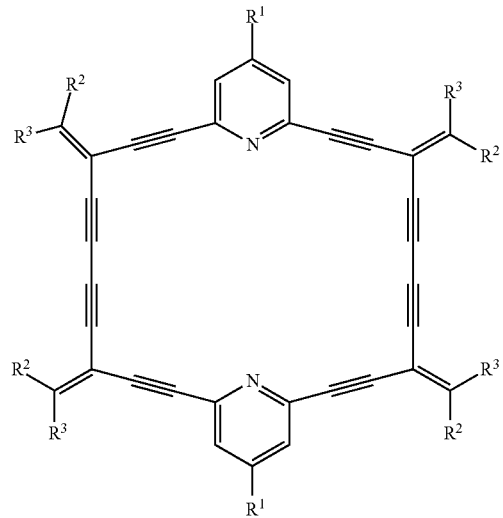

Formula I with $R^1$, $R^2$, and $R^3$ each independently selected from an alkyl group or an aryl group.

In the catalyst of the present disclosure, preferably, $R^1$, $R^2$, and $R^3$ in Formula I are independently selected from hydrogen atom, methyl, ethyl, isopropyl, cyclopentyl, cyclohexyl, phenyl, o-methylphenyl, o-ethylphenyl, o-isopropylphenyl, 2,4-dimethylphenyl, 2,4-diethylphenyl, 2,4-diisopropylphenyl, 2,4-dibutylphenyl, 2,6-diisopropylphenyl, 2,6-dimethylphenyl, 2,6-diethylphenyl, 2,6-dibutylphenyl, 2,4,6-trimethylphenyl, 2,4,6-triethylphenyl, 2,4,6-triisopropylphenyl, naphthyl, anthryl, and biphenyl.

More preferably, $R^1$, $R^2$, and $R^3$ are each independently selected from hydrogen atom, methyl, ethyl, isopropyl, phenyl, 2,6-diisopropylphenyl, and naphthyl.

In the catalyst of the present disclosure, the dehydropyridine annulene-type ligand used is obtained according to the following reaction formula:

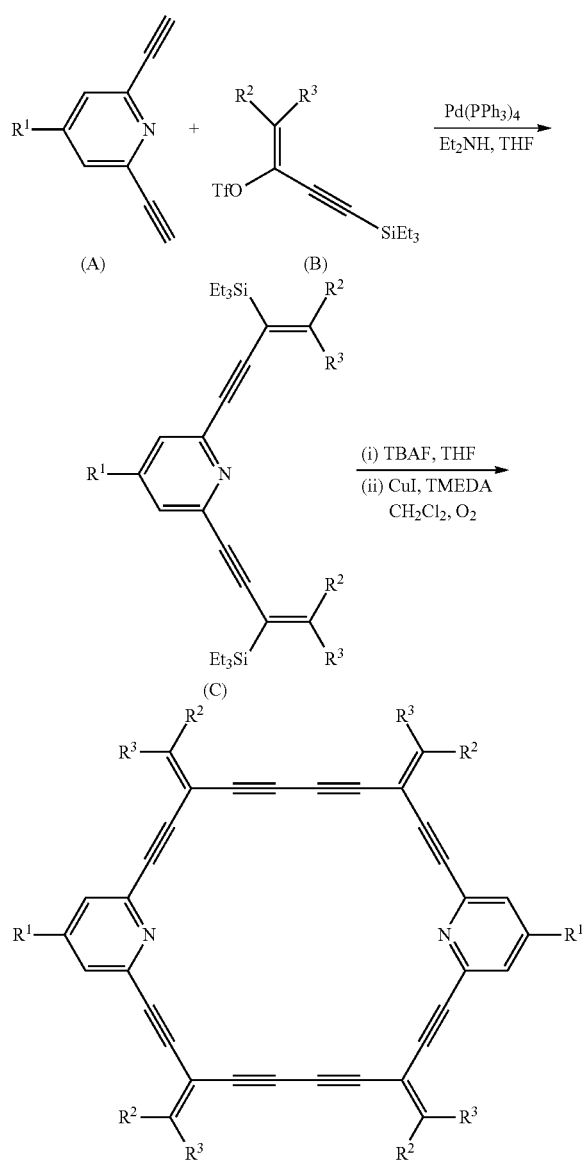

In the catalyst of the present disclosure, the dehydropyridine annulene-type ligand is obtained by a palladium-catalyzed cross-coupling reaction and a copper-catalyzed alkyne self-coupling reaction; and the specific preparation steps of the dehydropyridine annulene-type ligand used are as follows:

Tetrakis(triphenylphosphino)palladium and diethylamine are added to tetrahydrofuran, and the reactant A and the reactant B are successively added therein under stirring, and the mixture is heated under reflux for 12 hours, cooled, and filtered to obtain a solution of the intermediate C in tetrahydrofuran;

the tetrabutylammonium fluoride is added to the solution of intermediate C in tetrahydrofuran, stirred for 1 hour, and the solvent is removed; after methylene chloride is added to dissolve the mixture, copper iodide and tetramethylethylenediamine are further added, and the mixture is heated under reflux for 24 hours under air bubbling, and dehydropyridine annulene-type ligand was obtained by filtration, concentration and column chromatography separation.

In the catalyst of the present disclosure, preferably, the dehydropyridine annulene-type ligand consists of a plurality of compounds of Formula I. Among them, a plurality of compounds represented by the formula I are bonded together by a group, a chemical bond or an intermolecular force or the like. For example, a bridged, dendritic, and star-shaped compound may be obtained, or a polymerized polymer formed by binding to a polymer chain may be obtained.

In the catalyst of the present disclosure, preferably, the transition metal compound used is a compound of metal from Group IV B-VIII.

In the catalyst of the present disclosure, preferably, the transition metal compound used is a compound of chromium, molybdenum, tungsten, titanium, cobalt, tantalum, vanadium, zirconium, iron, nickel, or palladium.

More preferably, the transition metal compound used is a compound of chromium, zirconium, or titanium; more preferably, the transition metal compound is a compound of chromium.

In the catalyst of the present disclosure, preferably, the compound of chromium has a general formula of $CrR''_m$, wherein $R''$ is an organic anion or a neutral molecule, $R''$ contains 1-10 carbon atoms, and n is an integer of 1-6.

More preferably, $R''$ is an organic compound or a group thereof having a carboxyl group, a β-dione group, or a hydrocarbon group.

In the catalyst of the present disclosure, preferably, the compound of chromium used includes one or a combination of more of chromium acetate, chromium isooctanoate, chromium n-octanoate, chromium acetylacetonate, chromium diisoprene, diphenyl chromium, $CrCl_3(THF)_3$, $CrCl_2(THF)_2$, (phenyl)tricarbonylchromium, and hexacarbonylchromium.

More preferably, the compounds of chromium used is one or a combination of more of $CrCl_3(THF)_3$, chromium isooctanoate, and chromium acetylacetonate.

In the catalyst of the present disclosure, an organometallic compound acts as an activating agent. Preferably, the organometallic compound used is a compound containing a Group IIIA metal.

More preferably, the organometallic compounds used include one or a combination of more of an alkyl aluminum compound, an aluminoxane compound, an organoboron compound, an organic salt, an inorganic acid, and an inorganic salt.

In the catalyst of the present disclosure, preferably, the alkyl aluminum compound used includes an alkyl aluminum compound (particularly a trialkyl aluminum compound) and an aluminoxane compound.

More preferably, the alkyl aluminum compound used is triethyl aluminum, triisobutyl aluminum, tri-n-butyl aluminum, tri-n-hexyl aluminum, or tri-n-octyl aluminum; wherein the aluminoxane compound used is methyl aluminoxane, ethyl aluminoxane, isobutyl aluminoxane, and modified aluminoxane.

In the catalyst of the present disclosure, preferably, the molar ratio of the aluminoxane compound to the alkyl aluminum compound is 100-0.01:1, more preferably 10-0.1:1.

In the catalyst of the present disclosure, preferably, the alkyl aluminum compound used is alkyl aluminum halide, alkyl aluminum hydride, or alkyl aluminum sesquichloride.

More preferably, the alkyl aluminum compound used is $AlEt_2Cl$ and/or $Al_2Et_3Cl_3$.

In the catalyst of the present disclosure, preferably, the organic salt used is methyl lithium or methyl magnesium bromide.

In the catalyst of the present disclosure, preferably, the inorganic acid used is a tetrafluoroboric acid ether complex.

In the catalyst of the present disclosure, preferably, the inorganic salt used is tetrafluoroborate or hexafluoroantimonate.

In the catalyst of the present disclosure, preferably, the organoboron compound used includes one or a combination of more of boroxine, sodium borohydride, triethylborane, tris(pentafluorophenyl)boron, and tributylborate.

The catalyst for selective oligomerization of ethylene of the present disclosure utilizes the electronic effect of the substituent to adjust the charge distribution at the coordination point through the dehydropyridine annulene-type ligand having conductivity capability, and utilizes an interlayer molecular confinement effect formed by a dehydropyridine annulene-type ligand similar to a planar structure to obtain a catalyst having high activity and high selective ethylene oligomerization. In the existing ethylene selective tetramerization technology, most of the ligand structure uses P atom as an electron donating atom, and the metal center to catalyze selective oligomerization of ethylene, especially catalyzing ethylene tetramerization. Due to the unstable structure of the phosphine ligands, it is easy to decompose under the action of high temperature and alkyl aluminium and aluminoxane, resulting in catalyst variability or inactivation, so that the activity and selectivity of ethylene selective tetramerization are always difficult to achieve a high level. The dehydropyridine annulene-type ligand has a stable macrocyclic structure and can significantly transfer the electronic effect of the substituent group to the coordination hetero atom by conjugation to further enhance the stability of the metal complex and thereby significantly improve the catalytic activity.

The catalyst for selective oligomerization of ethylene of the present disclosure has an approximately planar structure of a ligand complexed with a metal compound to directly form a metal complex having a layered structure, and the inter-layer gap can achieve a molecular confinement effect on ethylene polymerization for the selective oligomerization of olefins, especially for the high selective preparation of 1-hexene and 1-octene.

The present disclosure also provides a method for selective oligomerization of ethylene using the catalyst for selective oligomerization of ethylene.

In the method of the present disclosure, preferably, the method is conducted by pre-mixing a dehydropyridine annulene-type ligand, a transition metal compound, and an organometallic compound before use; or directly adding a dehydropyridine annulene-type ligand, a transition metal compound, and an organometallic compound into a selective ethylene oligomerization reaction.

According to a particular embodiment of the present disclosure, when the dehydropyridine annulene-type ligand, the transition metal compound and the metal organic compound are premixed, the reaction may be carried out by a liquid phase reaction, such as under an action of a solvent, and solvents such as toluene, benzene and its derivatives can be selected and used; the reaction can be also carried out by a solid phase reaction;

According to a particular embodiment of the present disclosure, the dehydropyridine annulene-type ligand, the transition metal compound, and the metal organic compound can also be directly added to catalyze the oligomerization reaction by the in-situ reaction.

In the method of the present disclosure, preferably, the method is carried out in an inert solvent; more preferably, the inert solvent used is an alkyl hydrocarbon, anaromatic hydrocarbon, a halogenated hydrocarbon, an olefin, benzene, toluene, xylene, cumene, n-heptane, n-hexane, methylcyclohexane, cyclohexane, 1-hexene, 1-octene, or an ionic liquid.

In the method of the present disclosure, preferably, the method has a reaction temperature of from 0° C. to 200° C. and a reaction pressure of from 0.1 MPa to 50 MPa.

More preferably, the method has a reaction temperature of the method of from 50° C. to 200° C.

According to a particular embodiment of the present disclosure, the reaction conditions of the selective oligomerization reaction of ethylene can be adjusted according to a specific reaction, for example, the pressure for the ethylene tetramerization reaction is from 0.1 MPa to 50 MPa, preferably from 1.0 MPa to 10 MPa.

In the method of the present disclosure, preferably, the concentration of the catalyst for selective oligomerization of ethylene in the selective oligomerization reaction of ethylene is from 0.01 mol metal/L to 1000 mol metal/L, preferably 0.1 mol metal/L to 10 mol metal/L.

The catalyst for selective oligomerization of ethylene of the present disclosure can be used to catalyze the selective oligomerization reaction of ethylene; in particular, to catalyze selective trimerization and tetramerization reaction of ethylene.

When the catalyst for selective oligomerization of ethylene can be used to catalyze the selective oligomerization reaction of ethylene, the reaction temperature is from 0° C. to 200° C., and the reaction pressure is from 0.1 MPa to 50 MPa; preferably, the reaction temperature is from 50° C. to 200° C. The adjustment can be carried out according to the specific reaction. For example, the pressure of the ethylene tetramerization reaction is from 0.1 MPa to 50 MPa, preferably from 1.0 MPa to 10 MPa.

The concentration of the catalyst for selective oligomerization of ethylene in the selective oligomerization reaction of ethylene is from 0.01 mol metal/L to 1000 mol metal/L, preferably 0.1 mol metal/L to 10 mol metal/L.

The catalyst for selective oligomerization of ethylene has high activity, high selectivity of the target products 1-hexene and 1-octene, and low selectivity of 1-butene and 1-C10+.

The catalyst for selective oligomerization of ethylene has simple synthesis, low cost and long catalyst life, and the mass percentage of $C_6$-$C_8$ linear alpha-olefin in the product is >90%, and the mass percentage of $C_8$ linear alpha-olefin is >60%.

DETAILED DESCRIPTION

The technical solutions of the present disclosure are described in detail below in order to have a clearer understanding of the technical features, objectives and beneficial effects of the present disclosure, but it is not to be construed as limiting the scope of the disclosure.

Example 1

Firstly, this example provides a dehydropyridine annulene ligand L1 ($C_{84}H_{50}N_2$) which is prepared by the following steps.

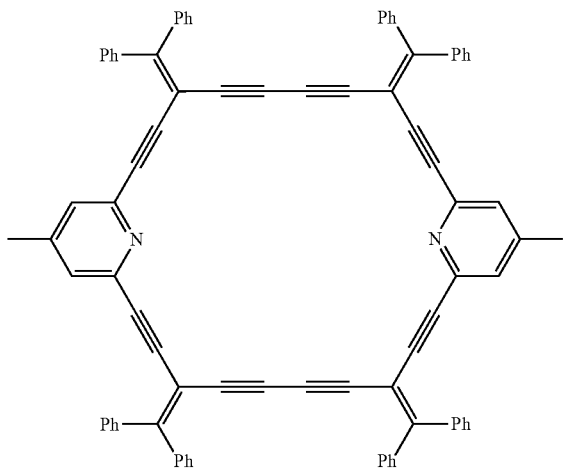

L1

0.12 g (0.1 mmol) of tetrakis(triphenylphosphino)palladium, 0.76 g (10.5 mmol) of diethylamine, 1.41 g (10.0 mmol) of 4-methyl-2,6-diacetylenylpyridine and 4.67 g (10.0 mmol) of 1,1-diphenyl-4-(triethyl silyl)-1-butene-3-yn-2-yl trifluoromethanesulfonate were successively added to 100 mL of tetrahydrofuran, stirred under reflux for 12 hours. The mixture is cooled, filtered to obtain a solution of the cross-coupling product in tetrahydrofuran.

Without separation and purification, 20 mL of undehydrated tetrabutylammonium fluoride saturated tetrahydrofuran solution was added to the above solution. After stirring at room temperature for 1 hour, the solvent was removed, and 100 mL of dichloromethane was added to dissolve the mixture, then 0.04 g (0.2 mmol) of copper iodide and 0.023 g (0.2 mmol) of tetramethylethylenediamine were added thereto, and the mixture was stirred under reflux for 24 hours. After finally filtering and concentrating, it was separated by n-hexane column chromatography to obtain 4.80 g (8.8 mmol, yield: 88.3%) of ligand L1.

This example also provides a catalyst for selective oligomerization of ethylene which is prepared by the following step:

Dehydrated methylcyclohexane (20 mL), DMAO (methylaluminoxane with trimethylaluminum removed) (0.57 g, 9.9 mmol), triethylaluminum (0.38 g, 3.3 mmol), ligand L1 (81 mg, 67.8 mol), $CrCl_3 \cdot (THF)_3$ (12 mg, 33 mol) were added to a 100 mL reactor equipped with stirrer with sufficient $N_2$ substitution, and the system was reacted at room temperature for 5 min for preparation.

The above-mentioned catalyst for selective oligomerization of ethylene of the present example is used for catalyzing ethylene oligomerization, and the specific steps are as follows:

The 500 mL autoclave was heated to a vacuum for 2 hours, replaced with nitrogen several rounds and charged with ethylene, cooled to a predetermined temperature, and the dehydrated methylcyclohexane (200 mL) and the above catalyst were added.

The oligomerization reaction was carried out at 45° C. and a pressure of 1 MPa. After 30 min of reaction, it was cooled in an ice bath, and the pressure was released. The reaction was terminated with an acidified ethanol having a mass fraction of 10% to obtain an oligomerized product of 61.1 g, and a catalyst activity being $3.7 \times 10^6$ g. oligomer/mol Cr·h. The distribution of oligomerized products is shown in Table 1.

Example 2

This Example was processed in a manner similar to Example 1, except that $R_1$ is —H. The oligomerized product obtained is 44.68 g, and the catalyst activity was $2.9 \times 10^6$ g oligomer/mol Cr·h. The distribution of oligomerized products is shown in Table 1.

Example 3

This Example was processed in a manner similar to Example 1, except that $R_2$, $R_3$ are methyl groups. The oligomerized product obtained is 84.15 g, and the catalyst activity is $5.1 \times 10^6$ g oligomer/mol Cr·h. The distribution of oligomerized products is shown in Table 1.

Example 4

This Example was processed in a manner similar to Example 1, except that $R_2$, $R_3$ are naphthyl groups. The oligomerized product obtained is 36.2 g, and the catalyst activity is $2.2 \times 10^6$ g oligomer/mol Cr·h. The distribution of oligomerized products is shown in Table 1.

Example 5

This Example was processed in a manner similar to Example 2, except that $R_2$, $R_3$ are isopropyl groups. The oligomerized product obtained is 103.95 g, and the catalyst activity is $6.3 \times 10^6$ g oligomer/mol Cr·h. The distribution of oligomerized products is shown in Table 1.

Example 6

This Example was processed in a manner similar to Example 5, except that $R_1$ is isopropyl group. The oligomerized product obtained is 115.5 g, and the catalyst activity is $7.0 \times 10^6$ g oligomer/mol Cr·h. The distribution of oligomerized products is shown in Table 1.

Example 7

This Example was processed in a manner similar to Example 2, except that $R_2$, $R_3$ are 2,6-diisopropylphenyl groups. The oligomerized product obtained is 100.65 g, and the catalyst activity is $6.1 \times 10^6$ g oligomer/mol Cr·h. The distribution of oligomerized products is shown in Table 1.

Example 8

This Example was processed in a manner similar to Example 2, except that the pressure of ethylene is 2 MPa. The oligomerized product obtained is 77.55 g, and the catalyst activity is $4.7 \times 10^6$ g oligomer/mol Cr·h. The distribution of oligomerized products is shown in Table 1.

Example 9

This Example was processed in a manner similar to Example 2, except that the pressure of ethylene is 4 MPa. The oligomerized product obtained is 120.45 g, and the catalyst activity is $7.3 \times 10^6$ g oligomer/mol Cr·h. The distribution of oligomerized products is shown in Table 1.

Example 10

This Example was processed in a manner similar to Example 2, except that the reaction temperature is 0° C. The oligomerized product obtained is 19.8 g, and the catalyst activity is $1.2 \times 10^6$ g oligomer/mol Cr·h. The distribution of oligomerized products is shown in Table 1.

Example 11

This Example was processed in a manner similar to Example 2, except that the reaction temperature is 90° C. The oligomerized product obtained is 72.6 g, and the catalyst activity is $4.4 \times 10^6$ g oligomer/mol Cr·h. The distribution of oligomerized products is shown in Table 1.

Example 13

This Example was processed in a manner similar to Example 9, except that the cocatalyst is MMAO. The oligomerized product obtained is 59.4 g and the catalyst activity is $3.6 \times 10^6$ g oligomer/mol Cr·h. The distribution of oligomerized products is shown in Table 1.

Example 14

This Example was processed in a manner similar to Example 9, except that the cocatalyst is MAO. The oligomerized product obtained is 46.2 g, and the catalyst activity is $2.8 \times 10^6$ g oligomer/mol Cr·h. The distribution of oligomerized products is shown in Table 1.

Example 15

This Example was processed in a manner similar to Example 9, except that the chromium compound is $CrCl_2(THF)_2$. The oligomerized product obtained is 18.2 g, and the catalyst activity is $1.1 \times 10^6$ g oligomer/mol Cr·h. The distribution of oligomerized products is shown in Table 1.

TABLE 1

Comparison of carbon number distribution of oligomerization products

| Carbon number distribution of products | $C_4$ (wt %) | $C_6$ (wt %) | $C_8$ (wt %) | $>C_{10}$ (wt %) | Content of $1\text{-}C_6^=$ $^a$(wt %) | Content of $1\text{-}C_8^=$ $^b$(wt %) |
|---|---|---|---|---|---|---|
| Example 1 | 5.44 | 38.25 | 55.29 | 1.02 | 92.31 | 95.21 |
| Example 2 | 4.54 | 34.57 | 59.54 | 1.35 | 90.22 | 96.51 |
| Example 3 | 4.01 | 34.01 | 59.84 | 2.14 | 91.03 | 94.57 |
| Example 4 | 6.35 | 37.35 | 52.57 | 3.73 | 94.21 | 95.68 |
| Example 5 | 6.37 | 37.24 | 54.32 | 2.07 | 89.32 | 97.51 |
| Example 6 | 3.03 | 35.68 | 59.72 | 1.57 | 88.21 | 96.32 |
| Example 7 | 8.25 | 33.24 | 55.85 | 2.66 | 95.14 | 97.01 |
| Example 8 | 2.04 | 33.41 | 63.57 | 0.98 | 85.12 | 96.34 |
| Example 9 | 3.24 | 22.76 | 72.58 | 1.42 | 82.01 | 95.14 |
| Example 10 | 2.57 | 27.62 | 68.54 | 1.27 | 83.25 | 94.57 |
| Example 11 | 4.68 | 69.57 | 23.70 | 2.05 | 97.65 | 93.67 |
| Example 12 | 2.54 | 37.87 | 56.35 | 3.24 | 92.54 | 96.57 |
| Example 13 | 3.65 | 34.57 | 57.76 | 4.02 | 91.47 | 96.08 |
| Example 14 | 1.17 | 36.78 | 59.66 | 2.39 | 97.38 | 97.51 |
| Example 15 | 7.35 | 42.69 | 48.19 | 1.77 | 93.65 | 95.88 |

Example 12

This Example was processed in a manner similar to Example 2, except that the amount of $CrCl_3 \cdot (THF)_3$ is 3 µmol. The oligomerized product obtained is 21.3 g and the catalyst activity is $14.2 \times 10^6$ g oligomer/mol Cr·h. The distribution of oligomerized products is shown in Table 1.

In Table 1, a means the percentage content of 1-C6= in C6, and b means the percentage content of 1-C8= in C8. C6=, C8= represents an olefin having a double bond at its end.

Table 2 shows the experimental conditions and catalyst activities of Example 1 to Example 15, wherein (a) is a dehydropyridine annulene-type ligand, (b) is a transition metal compound, and (c) is an organometallic compound.

TABLE 2

| Example | $R^1$ | $R^2$ | $R^3$ | Cocatalyst | Chromium compound |
|---|---|---|---|---|---|
| 1 | Methyl | Phenyl | Phenyl | DMAO/Et$_3$Al | CrCl$_3$•(THF)$_3$ |
| 2 | —H | Phenyl | Phenyl | DMAO/Et$_3$Al | CrCl$_3$•(THF)$_3$ |
| 3 | Methyl | Methyl | Methyl | DMAO/Et$_3$Al | CrCl$_3$•(THF)$_3$ |
| 4 | Methyl | Naphthyl | Naphthyl | DMAO/Et$_3$Al | CrCl$_3$•(THF)$_3$ |
| 5 | —H | Isopropyl | Isopropyl | DMAO/Et$_3$Al | CrCl$_3$•(THF)$_3$ |
| 6 | Isopropyl | Isopropyl | Isopropyl | DMAO/Et$_3$Al | CrCl$_3$•(THF)$_3$ |

TABLE 2-continued

| | | | | | |
|---|---|---|---|---|---|
| 7 | —H | 2,6-Diisopropylphenyl | 2,6-Diisopropylphenyl | DMAO/Et$_3$Al | CrCl$_3$•(THF)$_3$ |
| 8 | —H | Phenyl | Phenyl | DMAO/Et$_3$Al | CrCl$_3$•(THF)$_3$ |
| 9 | —H | Phenyl | Phenyl | DMAO/Et$_3$Al | CrCl$_3$•(THF)$_3$ |
| 10 | —H | Phenyl | Phenyl | DMAO/Et$_3$Al | CrCl$_3$•(THF)$_3$ |
| 11 | —H | Phenyl | Phenyl | DMAO/Et$_3$Al | CrCl$_3$•(THF)$_3$ |
| 12 | —H | Phenyl | Phenyl | DMAO/Et$_3$Al | CrCl$_3$•(THF)$_3$ |
| 13 | —H | Phenyl | Phenyl | MMAO | CrCl$_3$•(THF)$_3$ |
| 14 | —H | Phenyl | Phenyl | MAO | CrCl$_3$•(THF)$_3$ |
| 15 | —H | Phenyl | Phenyl | DMAO/Et$_3$Al | CrCl$_2$•(THF)$_2$ |

| Example | Reaction temperature (° C.) | Reaction pressure (MPa) | Catalyst concentration (mmol Cr/L) | (a) Added amount μmol | (b) Added amount μmol | (c) Added amount mmol | Catalyst activity $10^6$ g oligomer/mol Cr · h |
|---|---|---|---|---|---|---|---|
| 1 | 45 | 1 | 0.16 | 67.8 | 33 | 9.9/3.3 | 3.7 |
| 2 | 45 | 1 | 0.16 | 67.8 | 33 | 9.9/3.3 | 2.9 |
| 3 | 45 | 1 | 0.16 | 67.8 | 33 | 9.9/3.3 | 5.1 |
| 4 | 45 | 1 | 0.16 | 67.8 | 33 | 9.9/3.3 | 2.2 |
| 5 | 45 | 1 | 0.16 | 67.8 | 33 | 9.9/3.3 | 6.3 |
| 6 | 45 | 1 | 0.16 | 67.8 | 33 | 9.9/3.3 | 7.0 |
| 7 | 45 | 1 | 0.16 | 67.8 | 33 | 9.9/3.3 | 6.1 |
| 8 | 45 | 2 | 0.16 | 67.8 | 33 | 9.9/3.3 | 4.7 |
| 9 | 45 | 4 | 0.16 | 67.8 | 33 | 9.9/3.3 | 7.3 |
| 10 | 0 | 1 | 0.16 | 67.8 | 33 | 9.9/3.3 | 1.2 |
| 11 | 90 | 1 | 0.16 | 67.8 | 33 | 9.9/3.3 | 4.4 |
| 12 | 45 | 1 | 0.015 | 6 | 3 | 0.9/0.3 | 14.2 |
| 13 | 45 | 4 | 0.16 | 67.8 | 33 | 9.9/3.3 | 3.6 |
| 14 | 45 | 4 | 0.015 | 67.8 | 33 | 13.2 | 2.8 |
| 15 | 45 | 1 | 0.16 | 67.8 | 33 | 1.1 | 1.1 |

The above examples demonstrate that the catalyst for selective oligomerization of ethylene has high activity, high selectivity of the target products 1-hexene and 1-octene, and low yield of 1-butene and 1-C$_{10}^+$.

What is claimed is:

1. A catalyst for selective oligomerization of ethylene, wherein the raw material for the catalyst consists of: a dehydropyridine annulene ligand, a transition metal compound, and an organometallic compound in a molar ratio of 1:0.5-100:0.1-5000; wherein the dehydropyridine annulene ligand has a structural formula as shown in Formula I:

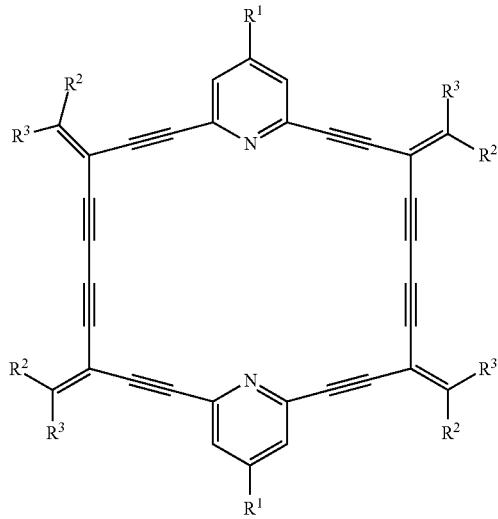

Formula I with $R^1$, $R^2$, $R^3$ each independently selected from an alkyl group or an aryl group, wherein the transition metal compound is a compound of a metal from Group IVB-VIIIB, and wherein the organometallic compound is a compound containing a Group IIIA metal.

2. The catalyst according to claim 1, wherein $R^1$, $R^2$, $R^3$ are independently selected from methyl, ethyl, isopropyl, cyclopentyl, cyclohexyl, phenyl, o-methylphenyl, o-ethylphenyl, o-isopropylphenyl, 2,4-dimethylphenyl, 2,4-diethylphenyl, 2,4-diisopropylphenyl, 2,4-dibutylphenyl, 2,6-diisopropylphenyl, 2,6-dimethylphenyl, 2,6-diethylphenyl, 2,6-dibutylphenyl, 2,4,6-trimethylphenyl, 2,4,6-triethylphenyl, 2,4,6-triisopropylphenyl, naphthyl, anthryl, and biphenyl.

3. The catalyst according to claim 1, wherein the dehydropyridine annulene ligand consists of a plurality of the compounds of Formula I.

4. The catalyst according to claim 1, wherein the transition metal compound is a compound of at least one or more of chromium, molybdenum, tungsten, titanium, cobalt, tantalum, vanadium, zirconium, iron, nickel, or palladium.

5. The catalyst according to claim 4, wherein the compound of chromium has a general formula of CrR''$_m$, wherein R'' is an organic anion or a neutral molecule, R'' contains 1-10 carbon atoms, and n is an integer of 1-6.

6. The catalyst according to claim 5, wherein the compound of chromium includes one or more of chromium acetate, chromium isooctanoate, chromium n-octanoate, chromium acetylacetonate, chromium diisoprene, diphenyl chromium, CrCl$_3$(THF)$_3$, CrCl$_2$(THF)$_2$, (phenyl)tricarbonylchromium, or hexacarbonylchromium.

7. The catalyst according to claim 1, wherein the organometallic compound includes one or more of an alkyl aluminum compound, an aluminoxane compound, an organoboron compound, and an organic salt.

8. The catalyst according to claim 7, wherein the alkyl aluminum compound includes an alkyl aluminum compound and an aluminoxane compound;

wherein the aluminoxane compound is methyl aluminoxane, ethyl aluminoxane, isobutyl aluminoxane, and modified aluminoxane; wherein the molar ratio of the aluminoxane compound to the alkyl aluminum compound is 100-0.01:1.

9. The catalyst according to claim 7, wherein the alkyl aluminum compound is one or more of alkyl aluminum halide, alkyl aluminum hydride, or alkyl aluminum sesquichloride.

10. The catalyst according to claim 7, wherein the organic salt is methyl lithium or methyl magnesium bromide; the inorganic acid is a tetrafluoroboric acid ether complex; the inorganic salt is tetrafluoroborate or hexafluoroantimonate; the organoboron compound includes one or more of boroxine, sodium borohydride, triethylborane, tris(pentafluorophenyl)boron, or tributylborate.

* * * * *